US010575976B2

(12) United States Patent
Bardach et al.

(10) Patent No.: US 10,575,976 B2
(45) Date of Patent: Mar. 3, 2020

(54) METHOD AND APPARATUS FOR WEIGHT MANAGEMENT UTILIZING AN INTRA-ORAL DEVICE

(71) Applicants: Dynamic Mouth Devices, L.L.C., Boonton, NJ (US); Salvatore Napoli, Florham Park, NJ (US)

(72) Inventors: Laura Bardach, Boonton, NJ (US); James Geduldig, Boonton, NJ (US); Salvatore Napoli, Boonton Township, NJ (US)

(73) Assignee: Dynamic Mouth Devices, L.L.C., Boonton, NJ (US)

( * ) Notice: Subject to any disclaimer, the term of this patent is extended or adjusted under 35 U.S.C. 154(b) by 654 days.

(21) Appl. No.: 14/700,569

(22) Filed: Apr. 30, 2015

(65) Prior Publication Data

US 2016/0317339 A1   Nov. 3, 2016

(51) Int. Cl.
*A61F 5/00* (2006.01)
*A61F 5/02* (2006.01)

(52) U.S. Cl.
CPC ............ *A61F 5/0006* (2013.01); *A61F 5/022* (2013.01)

(58) Field of Classification Search
CPC ...... A61F 5/56; A61F 5/566; A61F 2005/563; A61F 5/0006; A61F 5/0003;
(Continued)

(56) References Cited

U.S. PATENT DOCUMENTS 516,561 A    3/1894   Bosch
1,298,616 A   3/1919   Wilson
(Continued)

FOREIGN PATENT DOCUMENTS

AU           633269 B2    1/1993

OTHER PUBLICATIONS

"Effects of chewing gum on short-term appetite regulation in moderately restrained eaters", Appetite, Elsevier, 2011, pp. 475-482 (Year: 2011).*

(Continued)

*Primary Examiner* — Keri J Nelson
*Assistant Examiner* — Adam Baker
(74) *Attorney, Agent, or Firm* — Lerner, David, Littenberg, Krumholz & Mentlik, LLP

(57) ABSTRACT

An intra-oral device for weight management includes a carrier having a resiliently deformable protuberance on its outer surface. The protuberance may comprise a bite-pad having a height that varies along its length, with the apex being aligned with a first molar of a dental arch of the user. The protuberance may comprise a planar ridge structured and arranged to increase resistance to lateral movement of the user's jaw during a normal chewing cycle. Multiple resiliently deformable protuberances may include a bite-pad and a planar ridge on a buccal side of the bite-pad. Either or both of the bite-pad and planar ridge may be provided with an uneven, textured exterior surface. A method for promoting weight management may include positioning the carrier over an arch of teeth of the user instead of eating. The method may further include chewing on the carrier so as to deform the protuberance.

15 Claims, 7 Drawing Sheets

(58) Field of Classification Search
CPC ... A63B 71/085; A63B 71/086; A63B 71/088; A63B 2071/086; A63B 23/032; A61C 5/14; A61C 7/08; A61C 9/0006; A61C 7/36; Y10S 602/902
USPC ........ 128/848, 861, 857, 859, 862; 602/902; 606/234, 235, 236; 604/77; 433/6, 7, 11, 433/19, 24, 140; 482/11, 13
See application file for complete search history.

(56) References Cited

U.S. PATENT DOCUMENTS

| | | | |
|---|---|---|---|
| 2,288,470 A | 6/1942 | Lorraine | |
| 2,514,844 A | 7/1950 | Cohen | |
| 2,612,165 A | 9/1952 | Szuderski | |
| 2,708,931 A * | 5/1955 | Freedland | A61B 1/24 |
| | | | 128/861 |
| 2,824,561 A | 2/1958 | Mueller | |
| 3,223,085 A | 12/1965 | Gores et al. | |
| 3,224,442 A | 12/1965 | Stubbs | |
| 3,250,272 A | 5/1966 | Greenberg | |
| 3,416,527 A | 12/1968 | Hoef | |
| 3,496,939 A * | 2/1970 | Odiaga | A61B 17/1114 |
| | | | 285/260 |
| 3,503,127 A | 3/1970 | Kasdin et al. | |
| 3,505,995 A | 4/1970 | Greenberg | |
| 3,532,091 A | 10/1970 | Lerman | |
| 3,587,590 A | 6/1971 | Hastings | |
| 3,600,807 A | 8/1971 | Sipos | |
| 3,818,906 A | 6/1974 | Stubbs | |
| 3,864,832 A * | 2/1975 | Carlson | A61C 5/90 |
| | | | 128/862 |
| 3,996,934 A | 12/1976 | Zaffaroni | |
| 4,044,762 A | 8/1977 | Jacobs | |
| 4,192,307 A | 3/1980 | Baer | |
| 4,193,407 A | 3/1980 | Edmark | |
| 4,327,725 A | 5/1982 | Cortese et al. | |
| 4,348,381 A | 9/1982 | Gaffar et al. | |
| 4,350,154 A | 9/1982 | Feldbau | |
| 4,447,164 A | 5/1984 | Berndt | |
| 4,554,154 A | 11/1985 | White | |
| 4,569,342 A | 2/1986 | von Nostitz et al. | |
| 4,681,542 A | 7/1987 | Baum | |
| 4,765,324 A | 8/1988 | Lake, Jr. | |
| 4,920,984 A | 5/1990 | Furumichi et al. | |
| 4,935,225 A | 6/1990 | Curtis et al. | |
| 4,944,947 A | 7/1990 | Newman | |
| 5,015,628 A | 5/1991 | Reynolds | |
| 5,021,053 A | 6/1991 | Barclay et al. | |
| 5,052,410 A | 10/1991 | Stubbs | |
| 5,071,657 A | 12/1991 | Oloff et al. | |
| 5,082,007 A | 1/1992 | Adell | |
| 5,085,585 A | 2/1992 | Zimble | |
| 5,127,903 A | 7/1992 | Mailot et al. | |
| 5,152,301 A * | 10/1992 | Kittelsen | A63B 71/085 |
| | | | 128/846 |
| 5,194,003 A | 3/1993 | Garay et al. | |
| 5,200,194 A | 4/1993 | Edgren et al. | |
| 5,252,692 A | 10/1993 | Lovy et al. | |
| 5,286,490 A | 2/1994 | Grodberg | |
| 5,293,880 A * | 3/1994 | Levitt | A63B 71/085 |
| | | | 128/861 |
| 5,300,089 A | 4/1994 | Sassin | |
| 5,313,960 A * | 5/1994 | Tomasi | A61F 5/566 |
| | | | 128/848 |
| 5,323,787 A | 6/1994 | Pratt | |
| 5,339,832 A | 8/1994 | Kittelsen et al. | |
| 5,346,935 A | 9/1994 | Suzuki et al. | |
| 5,365,624 A | 11/1994 | Berns | |
| 5,366,935 A | 11/1994 | Alim et al. | |
| 5,395,392 A | 3/1995 | Suhonen | |
| 5,460,527 A | 10/1995 | Kittelsen | |
| 5,562,895 A | 10/1996 | Tung | |
| 5,566,684 A | 10/1996 | Wagner | |
| 5,620,011 A | 4/1997 | Flowers | |
| 5,810,886 A | 9/1998 | Hassan | |
| 5,819,744 A | 10/1998 | Stoyka, Jr. | |
| 5,826,581 A | 10/1998 | Yoshida | |
| 5,834,427 A | 11/1998 | Han et al. | |
| 5,842,860 A | 12/1998 | Funt | |
| 5,895,641 A | 4/1999 | Usen et al. | |
| 5,899,691 A * | 5/1999 | Parker | A63B 23/032 |
| | | | 128/861 |
| 5,924,422 A | 7/1999 | Gustafson | |
| 5,925,372 A | 7/1999 | Berner et al. | |
| 5,979,449 A | 11/1999 | Steer | |
| 5,980,249 A | 11/1999 | Fontenot | |
| 5,981,475 A | 11/1999 | Reynolds | |
| 5,993,413 A | 11/1999 | Aaltonen et al. | |
| 6,012,919 A | 1/2000 | Cross, III et al. | |
| 6,036,487 A | 3/2000 | Westerman | |
| 6,036,944 A | 3/2000 | Winston et al. | |
| 6,068,475 A | 5/2000 | Stoyka, Jr. | |
| 6,082,363 A | 7/2000 | Washburn | |
| 6,126,678 A | 10/2000 | Aaltonen et al. | |
| 6,203,566 B1 | 3/2001 | Alanen et al. | |
| 6,209,133 B1 | 4/2001 | Hinshaw | |
| 6,210,699 B1 | 4/2001 | Acharya et al. | |
| 6,244,269 B1 | 6/2001 | Tyler | |
| 6,257,239 B1 * | 7/2001 | Kittelsen | A63B 71/085 |
| | | | 128/859 |
| 6,269,816 B1 | 8/2001 | Rigonatti et al. | |
| 6,321,752 B1 | 11/2001 | Spottiswoode | |
| 6,412,489 B1 | 7/2002 | Sue | |
| 6,447,536 B1 | 9/2002 | Hinshaw | |
| 6,494,210 B1 | 12/2002 | Mams | |
| 6,505,625 B1 * | 1/2003 | Uenishi | A61C 7/08 |
| | | | 128/848 |
| 6,505,626 B2 | 1/2003 | Kittelsen et al. | |
| 6,514,176 B1 | 2/2003 | Norton | |
| 6,519,781 B1 | 2/2003 | Berns | |
| 6,553,996 B2 | 4/2003 | Kittelsen et al. | |
| 6,575,999 B1 | 6/2003 | Rohrig | |
| 6,581,604 B2 | 6/2003 | Cook | |
| 6,592,860 B1 | 7/2003 | Levy et al. | |
| 6,635,281 B2 | 10/2003 | Wong et al. | |
| 6,660,029 B2 | 12/2003 | VanSkiver et al. | |
| 6,675,806 B2 | 1/2004 | Kittelsen et al. | |
| 6,675,807 B2 * | 1/2004 | Kittelsen | A63B 71/085 |
| | | | 128/859 |
| 6,691,710 B2 | 2/2004 | Kittelsen et al. | |
| 6,752,824 B2 | 6/2004 | Yancy | |
| 7,001,357 B2 | 2/2006 | Berry, Sr. | |
| 7,118,376 B2 | 10/2006 | Jodaikin et al. | |
| 7,328,706 B2 | 2/2008 | Bardach et al. | |
| 7,500,984 B2 | 3/2009 | Fuisz et al. | |
| 7,506,651 B2 * | 3/2009 | Anonsen | B63C 11/186 |
| | | | 128/846 |
| 7,549,423 B1 * | 6/2009 | Hirshberg | A63B 71/085 |
| | | | 128/848 |
| 7,775,214 B1 * | 8/2010 | Lesniak | A63B 71/085 |
| | | | 128/846 |
| 8,181,655 B2 | 5/2012 | Bardach et al. | |
| 8,196,587 B2 * | 6/2012 | Chodorow | A61F 5/566 |
| | | | 128/861 |
| 8,215,312 B2 * | 7/2012 | Garabadian | A61F 5/566 |
| | | | 128/846 |
| 8,505,541 B2 | 8/2013 | Bardach et al. | |
| 8,900,614 B2 | 12/2014 | Bardach et al. | |
| 8,920,163 B2 * | 12/2014 | Farrell | A61F 5/566 |
| | | | 433/6 |
| 8,978,659 B2 | 3/2015 | Bardach et al. | |
| 9,022,903 B2 * | 5/2015 | Rafih | A63B 71/085 |
| | | | 482/121 |
| 2003/0031630 A1 | 2/2003 | Reznick et al. | |
| 2003/0176891 A1 | 9/2003 | Frederic | |
| 2003/0205234 A1 | 11/2003 | Bardach et al. | |
| 2005/0175959 A1 | 8/2005 | Jodaikin et al. | |
| 2006/0155331 A1 | 7/2006 | Bohmer | |
| 2006/0185679 A1 | 8/2006 | Costigan et al. | |
| 2007/0048347 A1 * | 3/2007 | Bardach | A61F 5/0006 |
| | | | 424/423 |
| 2007/0084471 A1 | 4/2007 | Napoli et al. | |

(56) References Cited

U.S. PATENT DOCUMENTS

| | | | |
|---|---|---|---|
| 2008/0044797 A1 | 2/2008 | Bardach et al. | |
| 2009/0035729 A1* | 2/2009 | Pele | A61F 5/0006 433/229 |
| 2011/0094522 A1* | 4/2011 | Weisflog | A61C 7/36 128/861 |
| 2011/0174319 A1* | 7/2011 | Busciglio | A61F 5/566 128/862 |
| 2012/0312309 A1* | 12/2012 | Zimmerman | A63B 71/085 128/861 |
| 2013/0118507 A1* | 5/2013 | Chappuis | A61B 17/24 128/859 |
| 2014/0352704 A1* | 12/2014 | Farrell | A63B 71/085 128/862 |
| 2015/0040917 A1* | 2/2015 | Gottsch | A63B 71/085 128/862 |
| 2015/0051585 A1 | 2/2015 | Bardach et al. | |
| 2015/0157434 A1 | 6/2015 | Bardach et al. | |
| 2017/0231723 A1* | 8/2017 | Lucas | A61C 7/08 433/6 |

OTHER PUBLICATIONS

Ohmure et al., "Mastication Suppresses Initial Gastric Emptying by Modulating Gastric Activity", J Dent Res 91(3):293-298, 2012.
Shimazaki et al., "Comparison of Brain Activation via Tooth Stimulation", J Dent Res 91(8):759-763, 2012.

* cited by examiner

METHOD AND APPARATUS FOR WEIGHT MANAGEMENT UTILIZING AN INTRA-ORAL DEVICE

FIELD OF THE INVENTION

The present invention relates to a method and apparatus for weight management including an intra-oral device that is worn on an arch of teeth and that is adapted to participate in the modulation of eating behavior.

BACKGROUND OF THE INVENTION

There is a growing concern about weight management in the United States and worldwide. The adverse health risks of overweightness and obesity are well known and include increased risk of coronary heart disease, cancer, stroke, high blood pressure, gallbladder and liver disease, osteoarthritis, gout, Metabolic Syndrome and diabetes.

Metabolic Syndrome is a major public health crisis, globally. It is characterized by a group of metabolic risk factors in one person, including: central obesity (excessive fat tissue in and around the abdomen); atherogenic dyslipidemia (blood fat disorders that foster plaque buildups in artery walls); raised blood pressure; insulin resistance or glucose intolerance; prothrombotic state; and proinflammatory state. The underlying causes of this syndrome are overweightness and obesity, physical inactivity and genetic factors. People with the metabolic syndrome are at increased risk of coronary heart disease, other diseases related to plaque buildups in artery walls like stroke and peripheral vascular disease, and type 2 diabetes.

Despite the fact that these health risks are well known, overweightness and obesity are prevalent in the United States. It is estimated that over 60% of American adults are overweight, meaning weighing more than is normal or necessary, especially having more body weight than is considered healthy for one's age, height, sex or build, or having a body mass index (BMI) of 25 to 29.9. Even more alarming, over 25% of American adults are obese. Obesity is defined as having a BMI of 30 or higher. BMI is a mathematical formula based on a person's height and weight. BMI is widely used by health care providers in determining whether a person is overweight or obese because it is closely associated with the measure of body fat, and may predict the development of health problems related to excess weight.

Generally, weight gain occurs when a person consumes more calories than he or she burns. Genetic, environmental, sociological and psychological factors contribute to weight gain, and consequently, overweightness or obesity. Several studies have shown that heredity is linked to obesity. Environmental and sociological factors also influence weight management inasmuch as lifestyle behaviors such as what a person eats and his or her level of physical activity directly influence the amount of calories consumed and burned.

Psychological factors have a significant affect on eating habits. Many people eat in response to negative emotions such as boredom, sadness, loneliness, depression, anxiety, anger and stress. This is referred to as "emotional eating." Many of these people eat, even when they are not physiologically hungry at all. Weight gain is a natural consequence of this overeating.

Overeating is a significant cause of overweightness. It is believed that there are three interconnected neurological anatomic nexuses that regulate food intake. The nexuses are the hunger center, which is located in the hypothalamus section of the brain, the appetite center, located in the brain stem, and the satiety center, which is connected to the hunger center and the appetite center. This feedback complex is further modulated by adipose tissue, endocrine organs and other humoral factors.

The hunger center is involved in the long term, metabolic regulation of food intake over weeks and months, and controls physiological hunger. When the human body actually requires nutrients, it will manifest this need with hunger or the stomach sensations we all identify as hunger.

Appetite, or the desire or inclination to eat, involves the short-term, environmental regulation of feeding from hour to hour over the course of a day. Appetite, as opposed to hunger, is a learned response to food and can be triggered by sensory cues at times when hunger is not present and eating is not required. Appetite may also be influenced by the psychological appeal of certain "eating behaviors" such as salivating, visualizing, smelling, tasting, chewing and swallowing food. When these eating behaviors have been satisfied, the desire to eat is abated. Many individuals eat when they are not hungry to satisfy their appetite.

It is extremely difficult for many people to lose weight of their own accord. Because one of the factors contributing to overweightness or obesity is psychological, medical treatment alone is often ineffective. Dieting can be successful in the short term, however, dieting is not effective for maintaining a desired weight long term. Most people who lose weight by dieting regain the weight they have lost, plus about ten extra pounds within five years. Behavior modification, i.e. changing habits relating to emotional eating, addresses the psychological factors that influence overeating and weight gain. There is a need for a successful method of promoting weight loss and weight management that provides an alternative to those who are compelled to eat when they are not hungry by providing the sensations necessary to satiate the appetite without the ill effects of excess calorie consumption.

A common method of treatment directed towards appetite suppression is administration of an appetite suppressant, in pill form. The drawbacks of this method of appetite suppression include peaks and troughs in the blood level of the active ingredient because the active ingredient is often not within a therapeutic range, psychological aversion to swallowing pills and user compliance where the pills must be taken at specific times. Another potential method of treatment directed towards appetite suppression is the intravenous, intramuscular or subcutaneous administration of agents that cannot be given enterically. The major drawback of this method of appetite suppression is the impracticality of self-administration. Another potential method of treatment directed towards appetite suppression is surgical alteration of various components of the gastrointestinal tract such as placation, stapling, bypass and other operations on the stomach and small intestines. The major drawback of surgical alteration techniques is a high degree of morbidity, and thus it is almost always reserved as a treatment of last resort. Therefore, an alternative method of suppressing appetite is needed.

Accordingly, the present invention contemplates new and improved methods of reducing weight and diminishing appetite that overcome the above-referenced problems and others.

SUMMARY OF THE INVENTION

One aspect of the present invention provides a method for promoting weight management. The method according to this aspect of the invention desirably includes, instead of eating, positioning an intra-oral device over at least a portion of a first arch of teeth of a user when the user has a desire to eat. The intra-oral device preferably includes a carrier that has a resiliently deformable protuberance along its outer surface.

According to one aspect of the invention, the method may further include the user chewing on the intra-oral device so as to deform the protuberance. According to another aspect of the invention, the method may further include removing the intra-oral device from the user's mouth when the user's desire to eat is extinguished.

According to further aspects of the invention, the carrier may have a channel configured to receive the portion of the user's first arch of teeth therein, which channel is defined by an outside wall, an inside wall, and an occlusal wall connecting them. According to that aspect of the invention, when the intra-oral device is positioned in an inserted position in which the channel receives the portion of the first arch of teeth, the protuberance is desirably positioned along the occlusal wall so as to contact at least one tooth of a second arch of teeth of the user. According to yet a further aspect of the invention, the carrier may be U-shaped such that the channel can receive substantially the entire first arch of teeth therein. According to another aspect of the invention, the outside wall of the carrier may include an opening adapted to expose a plurality of anterior teeth of the user's first arch of teeth received in the channel.

According to yet another aspect of the invention, the protuberance may comprise a bite-pad. According to one aspect of the invention, the height that the bite-pad projects above the occlusal wall may vary along the length of the bite-pad, with the maximum height preferably being in alignment with a first molar of the second arch of teeth. According to another aspect of the invention, the height of the bite-pad above the occlusal wall preferably defines an arcuate path. According to yet another aspect of the invention, an anterior end of the bite-pad may be aligned with a second premolar of the second arch of the user's teeth, and the posterior end of the bite-pad may be aligned with a second molar of the second arch.

In accordance with additional aspects of the invention, the protuberance may comprise a planar ridge. According to a further aspect of the invention, the planar ridge is desirably positioned and dimensioned so as to increase resistance to lateral movement of the user's jaw during a normal chewing cycle. According to another aspect of the invention, the carrier may have a resiliently deformable bite-pad protruding along an outer surface of the carrier, and the planar ridge may be located on a buccal side of the bite-pad. According to yet another aspect of the invention, the planar ridge may project higher above the occlusal wall than the bite-pad.

According to additional aspects of the invention, an outer surface of the protuberance may have an uneven, textured surface. Such textured surface may be comprised of a plurality of dome-shaped nodules, according to a further aspect of the invention. According to another aspect of the invention, the protuberance is preferably comprised of a different material than the carrier. According to that aspect of the invention, the protuberance may comprise an elastomeric material and the carrier may comprise a polymer having a higher rigidity than that elastomeric material.

Additional aspects of the invention provide an intra-oral device. The device according to this aspect of the invention desirably includes a carrier having a channel configured to receive at least a portion of a user's first arch of teeth therein, which channel is defined by an outside wall, an inside wall, and an occlusal wall connecting them. According to this aspect of the invention, the carrier preferably has a resiliently deformable protuberance comprising a bite-pad positioned along an outer surface of the occlusal wall. The height that the bite-pad projects above the occlusal wall may vary along the length of the bite-pad, with the maximum height preferably being in alignment with a first molar of a second arch of teeth of the user. According to a further aspect of the invention, an outer surface of the protuberance may have an uneven, textured surface.

Additional aspects of the invention provide an intra-oral device. The device according to this aspect of the invention desirably includes a carrier having a channel configured to receive at least a portion of a user's first arch of teeth therein, which channel is defined by an outside wall, an inside wall, and an occlusal wall connecting them. According to this aspect of the invention, the carrier preferably has a plurality of resiliently deformable protuberances positioned along an outer surface of the occlusal wall. According to this aspect of the invention, one of the protuberances may be a bite-pad and another one of the protuberances may be a planar ridge extending along the buccal side of the bite-pad and projecting above the occlusal wall higher than the bite-pad. According to a further aspect of the invention, an outer surface of either or both of the bite-pad and the planer ridge may have an uneven, textured surface.

BRIEF DESCRIPTION OF THE DRAWINGS

The above brief description as well as other objects, features and advantages of the present invention will be more fully appreciated by reference to the following detailed description of the presently preferred but nonetheless illustrative embodiments in accordance with the present invention when taken in conjunction with the accompanying drawings, which are not to scale, wherein.

DETAILED DESCRIPTION

It is noted that, for clarity, all reference numbers for specific teeth as used herein correspond to the numbers associated with those teeth as provided for in the Universal Numbering System commonly used in the United States.

Figure 1:
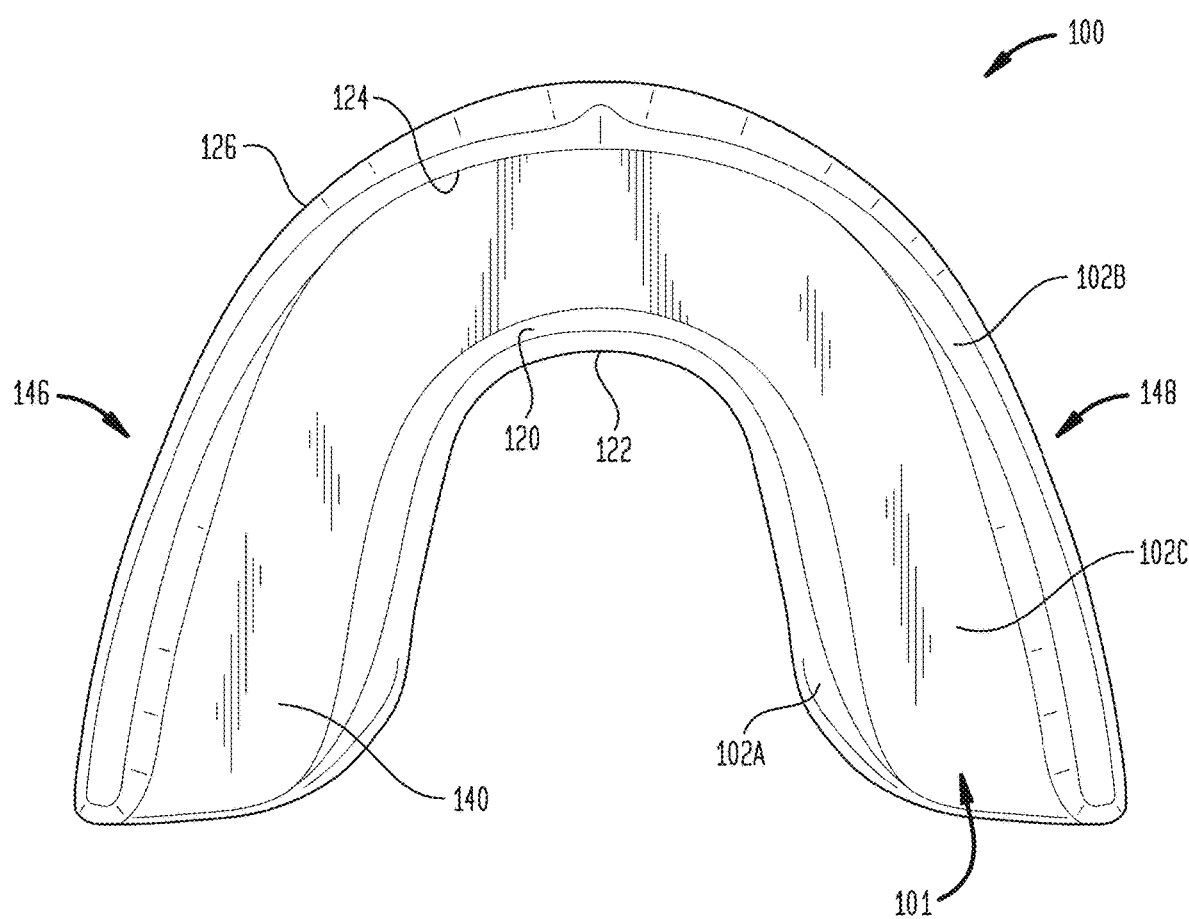
FIG. 1 is a top plan view of an intra-oral device in accordance with an embodiment of the present invention.

Referring to FIG. 1, a top plan view of an intra-oral device in accordance with one embodiment of the present invention is illustrated. The device includes a carrier 100 having a channel 101 serving as a recess for receiving an arch of teeth. Carrier 100 can be positioned over the user's upper (or maxillary) teeth or the user's lower (or mandibular) teeth. If the device is worn on the upper teeth, it may be referred to as a maxillary device. If the device is worn on the lower teeth, it may be referred to as a mandibular device. In one embodiment, the carrier 100 may be U-shaped, as shown in FIG. 1, and it may be dimensioned so as to receive substantially an entire arch of teeth. In other embodiments, the carrier may be shaped and dimensioned so as to receive only a portion of an arch of teeth.

Channel 101 is formed by an inside wall 102A, an outside wall 102B and an occlusal wall 102C. The inside wall 102A is referred to as the lingual/palatal wall. The inside wall 102A has an inner surface 120 and an outer surface 122. In a maxillary device, the inner surface 120 of the inside wall 102A touches the user's teeth, gingiva and palate, and the outer surface 122 of the inside wall 102A may touch the upper (dorsal) surface of the user's tongue. In a mandibular device, the inner surface 120 of the inside wall 102A touches the teeth, gingival and lingual surface of the dentoalveolar process, and the outer surface 122 of the inside wall 102A will touch the under-surface (ventral) of the tongue. The outside wall 102B is referred to as the buccal/labial wall. The outside wall 102B has an inner surface 124 and an outer surface 126. In a maxillary and mandibular device, the inner surface 124 of the outside wall 102B touches the user's gingival and teeth and the outer surface 126 of the outside wall 102B touches the user's cheeks and lips. The occlusal wall 102C connects the inside wall 102A to the outside wall 102B. The occlusal wall 102C has an inner surface 140 and an outer surface 142. In a maxillary device, the inner surface 140 of the occlusal wall 102C touches the occlusal surfaces of the maxillary teeth, and the outer surface 142 is oriented so as to come in contact with the occlusal surfaces of the mandibular teeth when the user's jaw is closed. In a mandibular device, the inner surface 140 of the occlusal wall 102C touches the occlusal surfaces of the mandibular teeth, and the outer surface 142 is oriented so as to come in contact with the occlusal surfaces of the maxillary teeth when the user's jaw is closed. Walls 102A, 102B, and 102C are collectively referred to as walls 102.

The intended material for carrier 100 may, for various embodiments, be any such material as is currently used in therapeutic intra-oral carriers or sports mouthguards. Mouthguards are typically made from plastic materials such as an ethylene vinyl acetate copolymer (EVA). Additives may be added to the EVA itself to provide special chemical or physical properties for different applications. In some embodiments of this device, flavoring and aromatic agents may be added to the polymer. Colorants, perfumes and softening agents may be added as well. For example, German patent 4011204 discloses a mouthguard material consisting of an EVA copolymer material, polycaprolactone, colorants, perfumes and polyvinyl acetate (PVA). The softening point of the resultant mouthguard is reduced for ease of manipulation and shaping.

Figure 2:
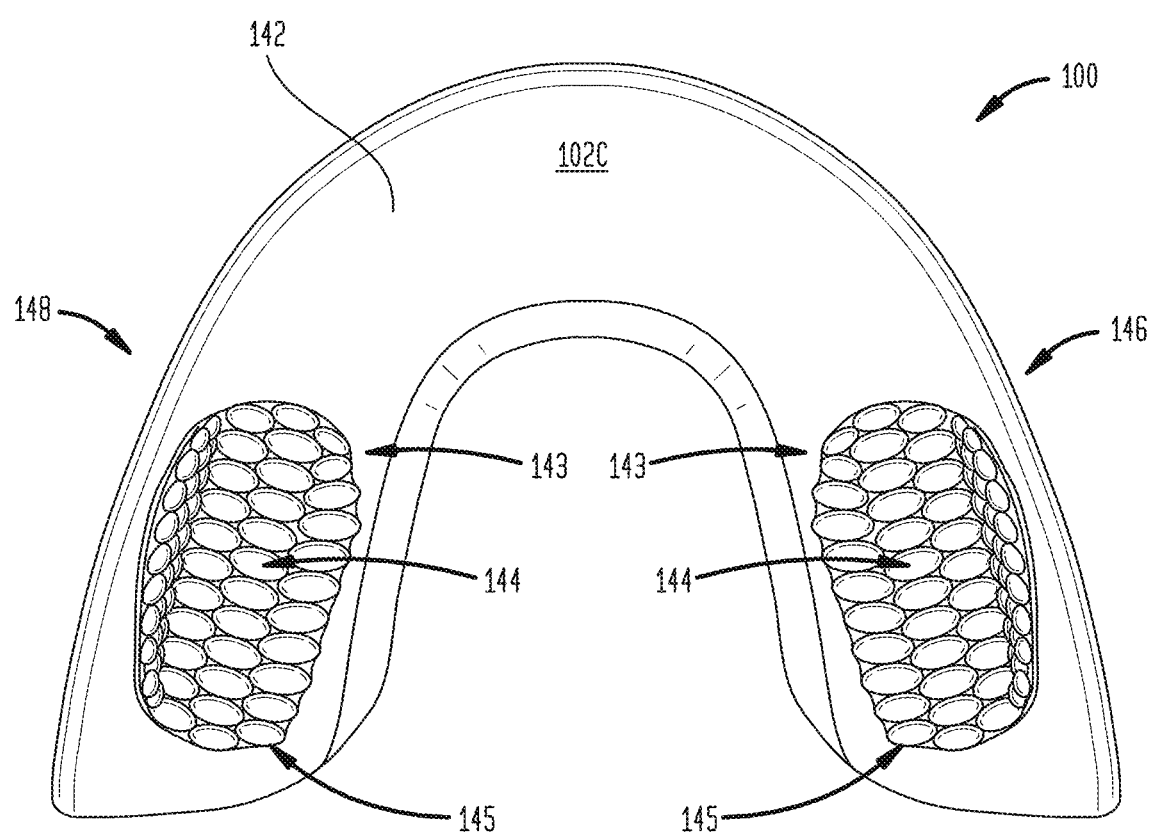
FIG. 2 is a bottom plan view of the intra-oral device of FIG. 1.
Figure 3:
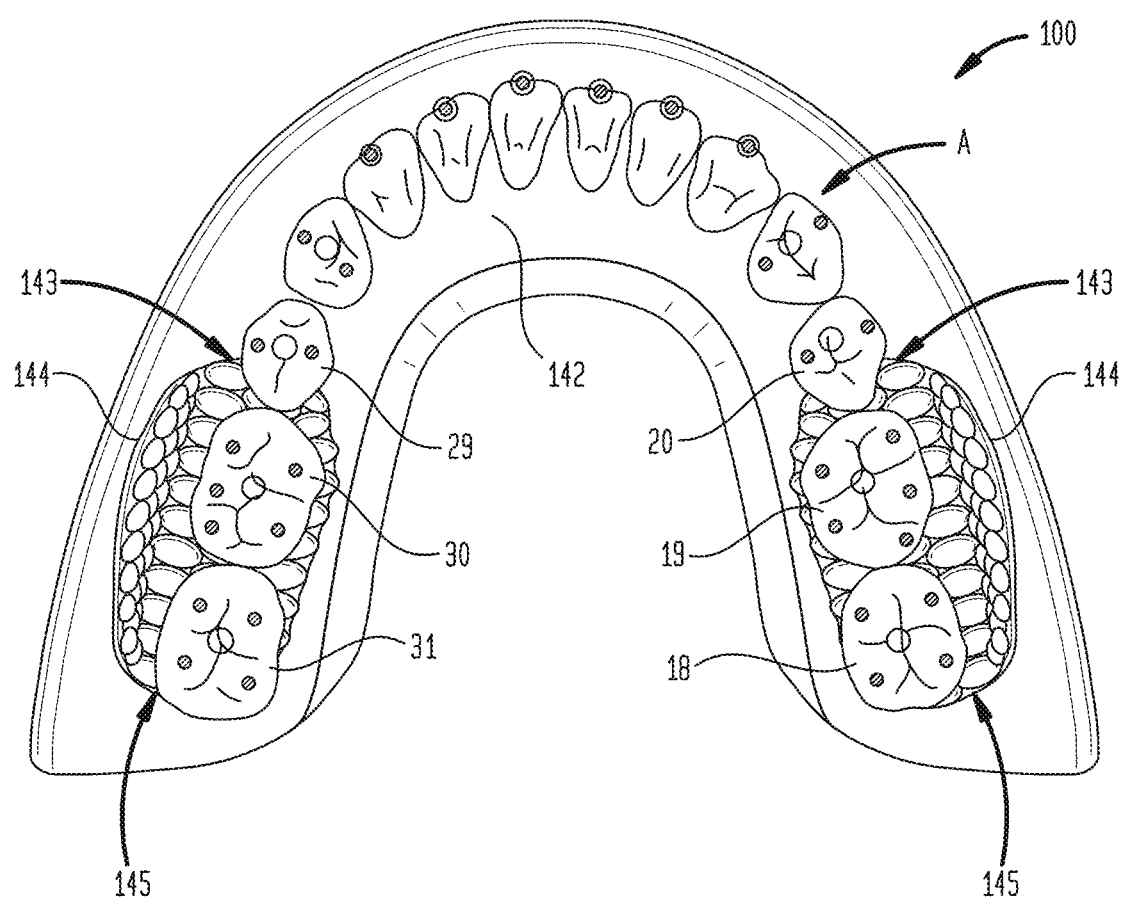
FIG. 3 is the bottom plan view of FIG. 2, showing the positioning of the device with respect to a mandibular dental arch.

As shown in FIG. 2, the outer surface 142 of the occlusal wall 102C of the carrier 100 includes dental engagement features 144 positioned on both the left side 146 and the right side 148 of the device. The features 144 desirably protrude above the outer surface 142 of the carrier 100 so as to come in contact with the teeth of the dental arch opposite to that which is received by the channel 101 of the carrier. Each dental engagement feature 144 extends along the outer surface 142 of the carrier 100 from an anterior end 143 to a posterior end 145 of the feature 144. For example, FIG. 3 illustrates an example of a carrier 100 used as a maxillary device, where the mandibular dental arch A is superimposed upon the carrier in the position in which it would contact the outer surface 142 when the user's jaw is closed. As shown, each dental engagement feature 144 may have an anterior end 143 aligned with the second premolar 20, 29 and a posterior end 145 aligned with the second molar 18, 31. Similarly, in an embodiment of a mandibular device, each dental engagement feature 144 may extend along the outer surface of the occlusal wall from the position of the second premolar of the maxillary teeth to the position of the second molar of the maxillary teeth. In other embodiments, however, the dental engagement features may be positioned in alignment with other teeth of the opposing dental arch, and the lengths of the features may be such that more or fewer teeth of that dental arch will contact the features.

The dental engagement features 144 are desirably formed of a deformable but resilient material so that they can be deformed by chewing action of the user. For example, the dental engagement features may be formed of an elastomeric material. Such elastomeric material may desirably have a Shore A hardness value in the range of 40 to 60. Preferable materials may include thermoplastic elastomers, such as those sold under the trademark Versaflex™ by PolyOne Corporation of McHenry, Ill.

The dental engagement features 144 may be secured to the outer surface 142 of the occlusal wall 102C of the carrier 100, or the features 144 may be secured within correspondingly shaped recesses within the occlusal wall 102C. In either case, the dental engagement features may be secured to the carrier 100 with a suitable adhesive. In the case where the dental engagement features 144 are received within corresponding recesses in the carrier 100, the features 144 may alternatively (or additionally) be secured to the carrier 100 by a snap fit, such as by having a projecting lip around all or portions of the recesses to retain the dental engagement features 144 within the respective recesses.

Figure 4:
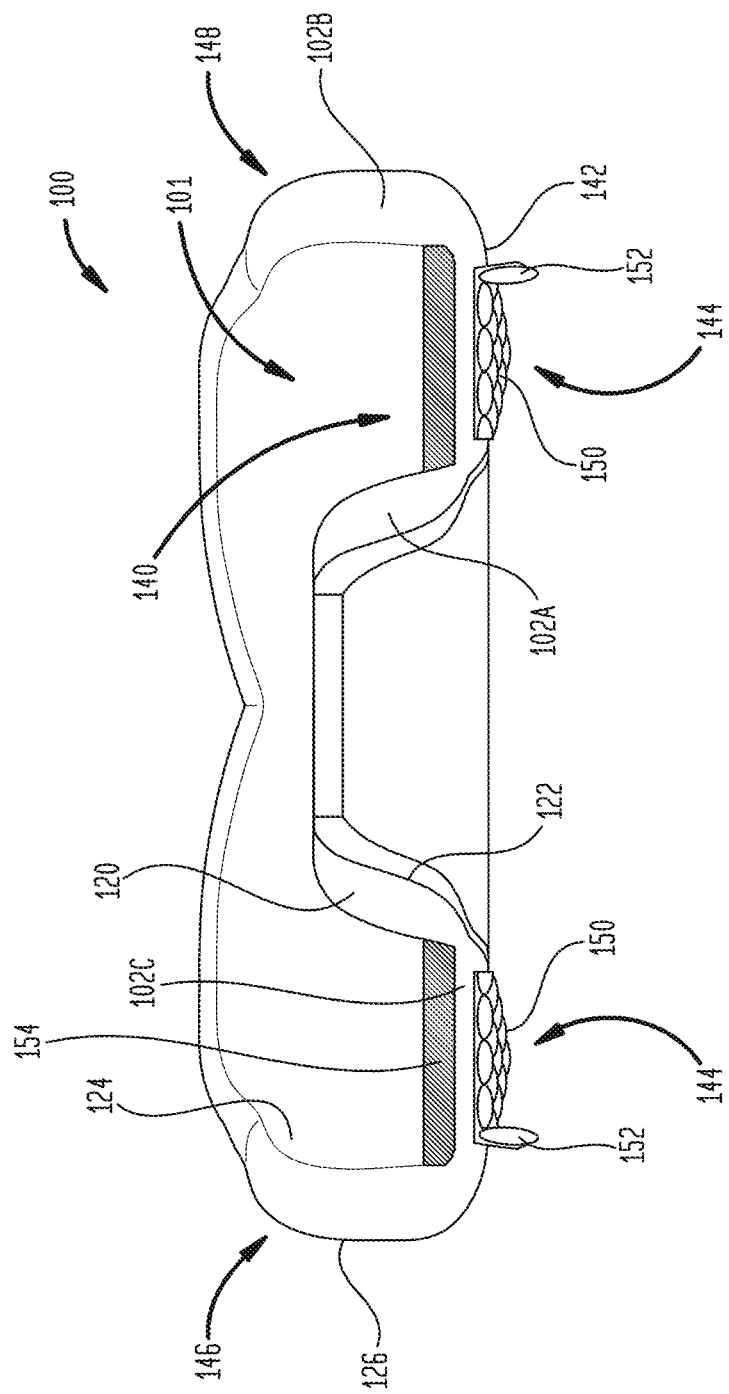
FIG. 4 is a rear elevational view the intra-oral device of FIG. 1.

As shown in FIG. 4, each dental engagement feature 144 may include a bite-pad 150 and a ridge 152. The bite-pad 150 is desirably aligned with the dental arch opposite that which is received by the channel 101 of the carrier 100, such that that opposing dental arch can compress the bite-pad 150 when the user's jaw is closed. The bite-pad 150 projects above the outer surface 142 of the occlusal wall 102C. Desirably, the height that the bite-pad 150 projects above the outer surface 142 varies along the length of the bite-pad 150 between the anterior end 143 and the posterior end 145 of the dental engagement feature 144. For example, the height of the bite-pad 150 may define an arcuate shape along its length. The bite-pad 150 may also define an arcuate shape along its width dimension. Preferably the apex (i.e., highest point) of the bite-pad 150 is aligned with the first molar 19, 30 of the opposing dental arch A. In that regard, it is believed that the first molars of both dental arches are the primary teeth at the somatosensory level participating in the satiety feedback mechanism. Thus, by having the bite-pad 150 of the intra-oral device apply maximum pressure to the first molars, it is believed that the present invention will provide maximal neuronal input to the feedback circuitry responsible for modulating feeding behaviors.

The ridge 152 of each dental engagement feature 144 is desirably structured as a generally planar projection extending from the outer surface 142 of the occlusal wall 102C. The ridge 152 is preferably positioned on the buccal side (i.e., closer to the outside wall 102B of the carrier 100) of the bite-pad 150. The ridge 152 may be contiguous with the bite-pad 150, or the ridge 152 may be at least slightly spaced apart from the bite-pad 150 The maximum height that the ridge 152 projects above the outer surface 142 is desirably higher than the apex of the bite-pad 150. The height and rigidity of the ridge 152 are desirably selected so as to increase resistance to lateral movement of the user's jaw during a normal chewing cycle. It is believed that the increased effort required to overcome the resistance imposed by the ridges 152 while maintaining a normal cadence in chewing will generate more activity in the muscles of mastication, which will desirably enhance the sensory feedback to the portions of the brain that regulate eating behavior as well as satiety and pleasure.

Figure 5:
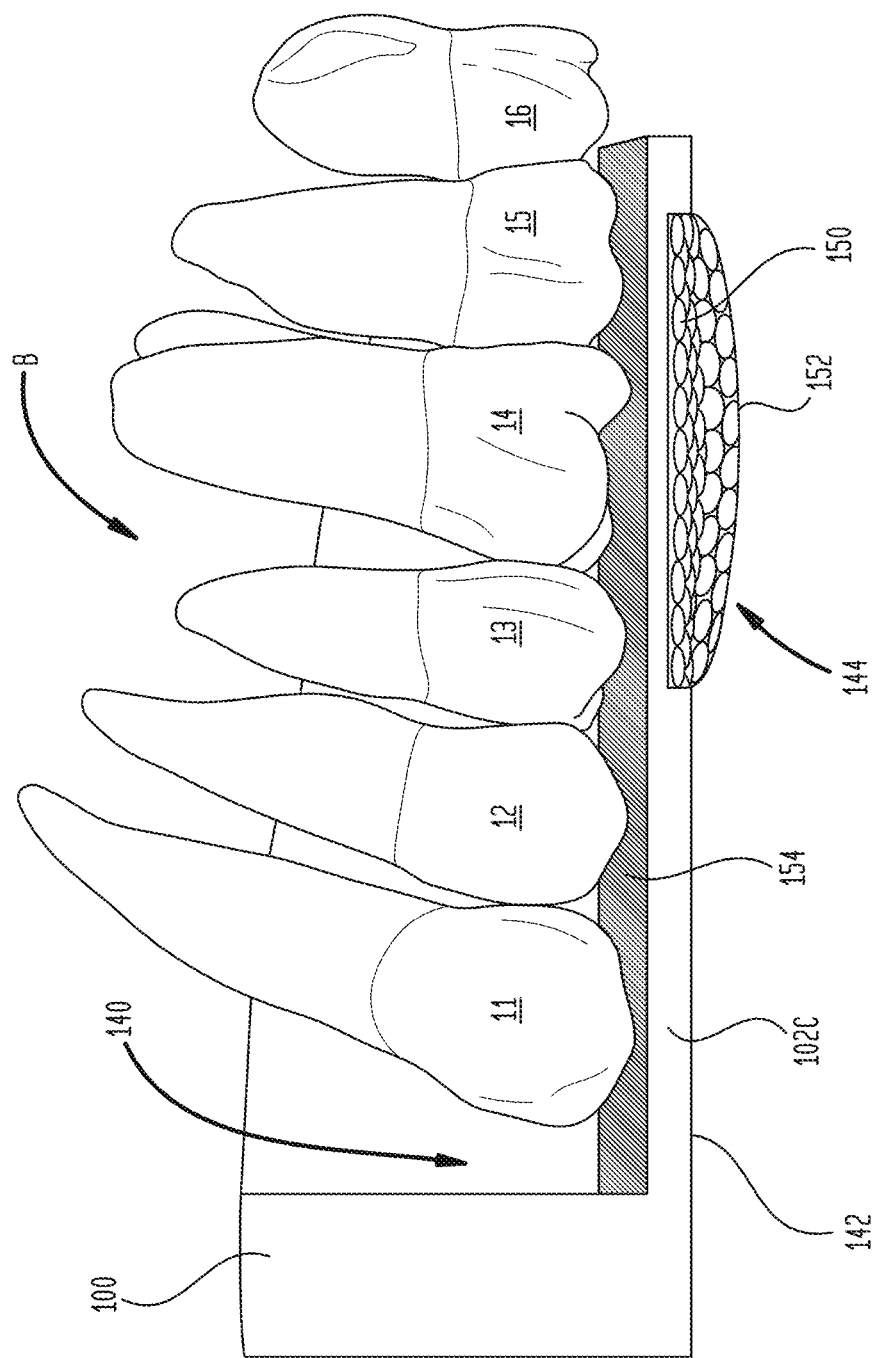
FIG. 5 is a side sectional view of a portion of the intra-oral device of FIG. 1, showing the positioning of the device with respect to a portion of a maxillary dental arch.
Figure 6:
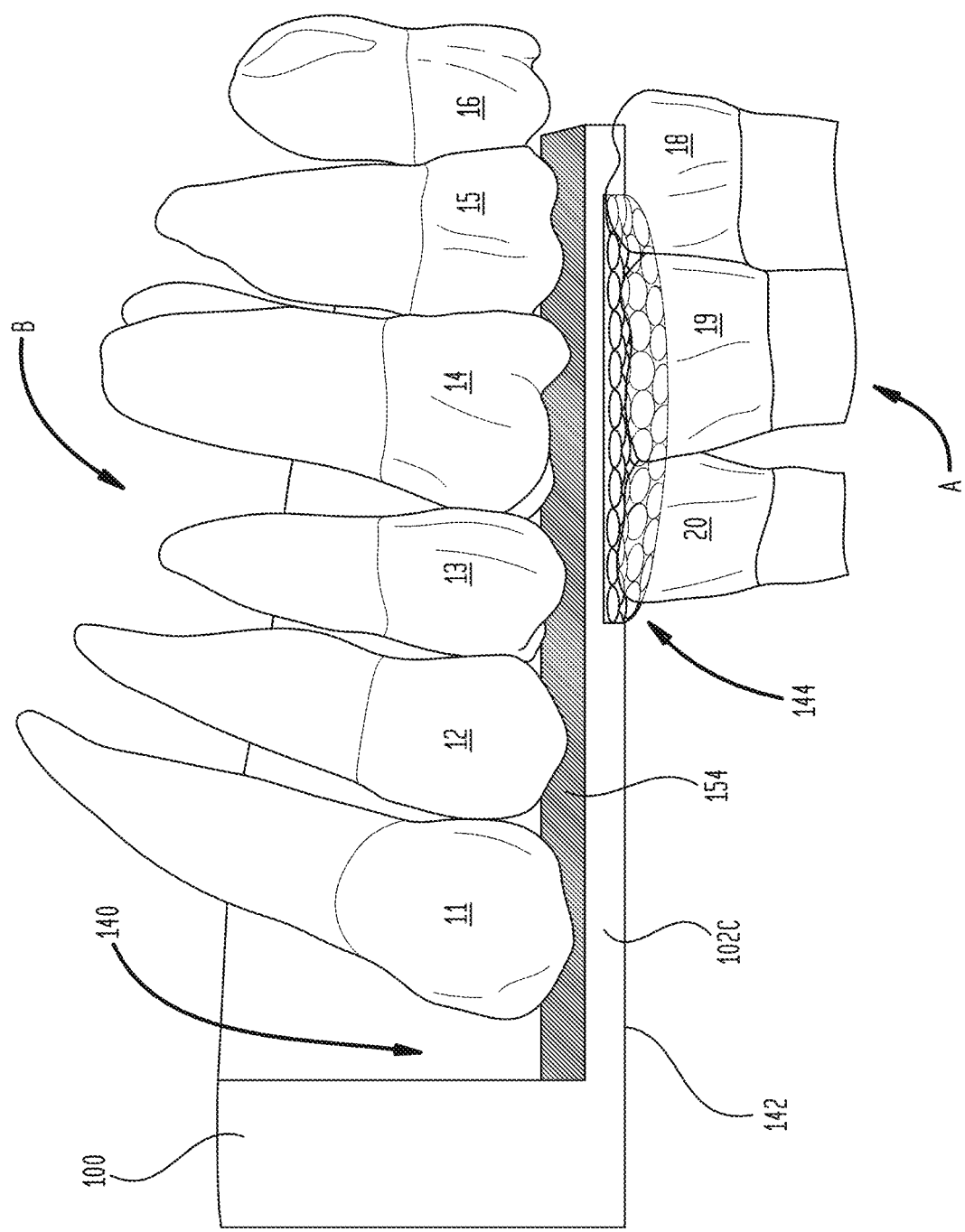
FIG. 6 is the side sectional view of FIG. 5, showing the positioning of the device with respect to maxillary and mandibular dental arches.

FIG. 5 illustrates a side sectional view of a portion of the carrier 100, with a portion of a maxillary dental arch B received within the channel 101. As shown in FIG. 5, the height of the ridge 152 above the outer surface 142 of the occlusal wall 102C may vary along the length of the ridge 152 between the anterior end 143 and the posterior end 145 of the dental engagement feature 144. For example, the height of the ridge 152 may define an arcuate shape along its length. FIG. 6 illustrates the side sectional view of the portion of the carrier 100 and the portion of the maxillary dental arch B illustrated in FIG. 5, and FIG. 6 further includes a portion of the mandibular dental arch A superimposed in a position in which the user's jaw is closed, such that certain teeth of the mandibular dental arch A contact the dental engagement feature 144. As shown in FIG. 6, those teeth may be the second molar 18, the first molar 19, and the second premolar 20. Also shown, for reference in FIGS. 5 and 6, are certain teeth of the maxillary dental arch B. Those teeth are a canine 11, a first premolar 12, a second premolar 13, a first molar 14, a second molar 15, and a third molar 16 of the maxillary arch B.

The bite-pad 150 and ridge 152 may have a variety of suitable dimensions, depending on the anatomy of the user's mouth. In one exemplary embodiment of the intra-oral device, the apex of the bite-pad 150 may be 0.25 mm above the outer surface 142, and the maximum height of the ridge 152 may be 2 mm above the outer surface. In another embodiment, the apex of the bite-pad 150 may be higher than 0.25 mm, with that height being determined by taking into account the deformability of the bite-pad 150 under different pressures and setting the height such that the molar to which the bite-pad 150 applies pressure will not be driven into its alveolar socket more than 0.25 mm, which is approximately the thickness of the periodontal ligament. In that way, occlusal injury may be avoided.

Desirably, either or both of the bite-pad 150 and the ridge 152 may include an uneven texture along their outer surfaces. Such texture is believed to stimulate tactile receptors in the mouth, which is believed to beneficially increase muscular activity. In additional embodiments (not shown), the outer surface 126 of the outside wall 102B may include such texture to take advantage of the numerous tactile receptors located within the buccal mucosa. Various textures may be used for any of the above-mentioned textured surfaces. For example, as shown in FIGS. 2-6, one preferred texture may comprise a plurality of dome-shaped nodules having a "bubbled" topology.

As shown in FIGS. 4-6, the inside of the channel 101 may include a chemically bonded low-temperature plastic layer 154 that deforms on heating to the temperature of boiling water (approximately 100 degrees Celsius). Such a layer may be useful in a "boil-and-bite" self-molding process, whereby the user places the carrier 100 into boiling water and then "bites" into the channel 101 of the carrier 100 to cause the low-temperature plastic layer 154 to mold and conform to the user's dentoalveolar structures. Although the low-temperature plastic layer 154 is illustrated along the inner surface 140 of the occlusal wall 102C, such layer may be located along any or all of the inner surfaces 120, 124, 140 along the channel 101.

In one exemplary embodiment, the thickness of the low-temperature plastic layer 154 is approximately 2 mm. The thickness of the occlusal wall 102C between that layer 154 and the outer surface 142 may be an additional 2 mm. In an embodiment in which the dental engagement features 144 are secured within recesses in the occlusal wall 102C, such recesses may be approximately 1 mm deep.

Figure 7:
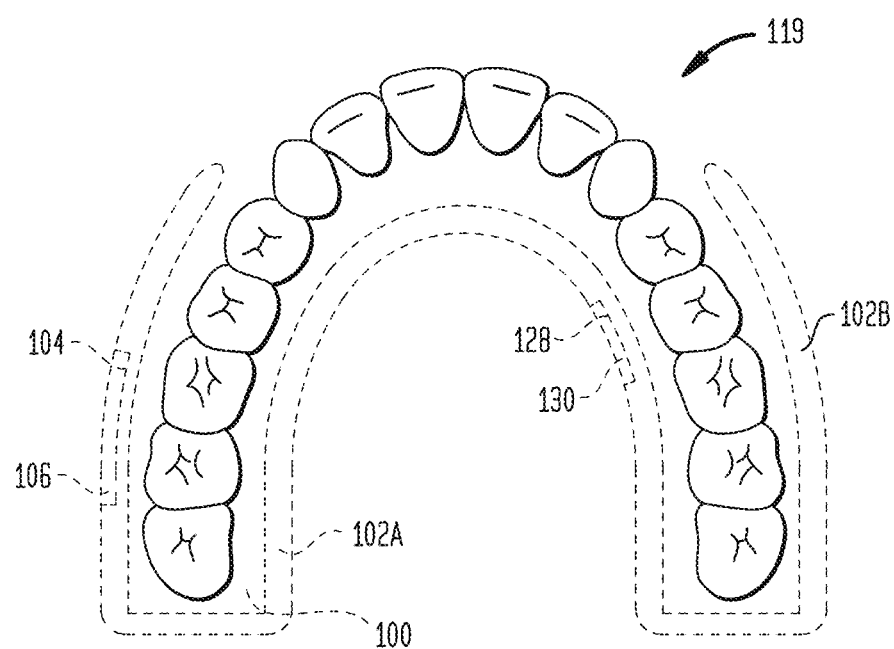
FIG. 7 is a top plan view of an intra-oral device in accordance with a second embodiment of the present invention, showing the positioning of the device with respect to an arch of teeth.

In accordance with other embodiments of the present invention, the dental engagement features 144 may be located on a carrier 100' having a different structure than that discussed above. In that regard, such alternative carrier 100' may have one or more of any of the structural features of the carriers disclosed in Applicants' own U.S. Pat. No. 8,900,614, issued on Dec. 2, 2014 (hereinafter "the '614 patent"), with the addition of one or more dental engagement features 144 as disclosed herein. For example, the carrier 100' may have one or more insets 104, 128 placed on the inner or outer surfaces of any of the walls 102 of the carrier 100' for use as either a maxillary or mandibular device, as illustrated in FIG. 7. The insets 104, 128 are desirably configured to receive respective inserts 106, 130, as disclosed in the '614 patent. The inserts 106, 130 may carry any one or more of the beneficial agents disclosed in the '614 patent. Blank inserts that do not carry a beneficial agent may also be adapted to fit the insets, such as to maintain the shape and integrity of the insets. In an embodiment wherein there are multiple insets, a combination of blank inserts and inserts carrying a beneficial agent may be utilized.

In accordance with further alternative embodiments, the carrier 100' may be generally U-shaped, but without the outside wall 102B extending to cover the front teeth, as also disclosed in the '614 patent. Beneficially, such a design may allow for inconspicuous wear. For example, as shown in FIG. 7, the outside wall of the U-shaped carrier 100' may have a gap 119. Typically, the gap 119 will be big enough so that the user's canines and incisors are visible, however, the size of the gap can vary. The inside wall 102A of the intra-oral device may be continuous so that the U-shape of the intra-oral device is maintained. However, in yet other alternative embodiments (not shown), the inside wall 102A need not be continuous, and instead the left and right sides of the carrier may not be connected at all, or they may be connected by a bridge portion extending between and connecting together the left and right sides of the carrier. For example, in a maxillary device, such a bridge portion may extend along (and may also conform to) the user's palate. In a mandibular device, the bridge portion may extend underneath the user's tongue.

Although, for illustrative purposes, the embodiment of the carrier 100' illustrated in FIG. 7 includes insets 104, 128 and inserts 106, 130 as well as an outside wall 102B does not extend to cover the front teeth, an embodiment of a carrier 100' in accordance with the present invention need not include all of such features. That is, an embodiment of a carrier 100' in which the outside wall 102B does not extend to cover the front teeth need not include insets 104, 128 and inserts 106, 130. Conversely, an embodiment of a carrier 100' having one or more insets 104, 128 and corresponding inserts 106, 130 need not be structured so as to expose the front teeth (e.g., by including a gap 119). Moreover, in yet further alternative embodiments of the carrier 100', any one or more of the beneficial agents disclosed in the '614 patent may be suffused into all or a portion of the material of the carrier 100' itself. The carrying of one or more beneficial agents in that manner may be instead of or in addition to carrying one or more beneficial agents in any inserts 106, 130 that may be included in such carrier 100'.

In any or all of the alternative embodiments of a carrier 100' discussed above, one or more dental engagement features 144 as disclosed herein may be included. For example, although not shown in FIG. 7, such features 144 may be located along the outer surface 142 of the occlusal wall 102C of the carrier 100', as discussed above in connection with the embodiment illustrated in FIGS. 1-6. Moreover, in any or all the alternative embodiments of a carrier 100' discussed above, a deformable low-temperature plastic layer 154 for use in a "boil-and-bite" self-molding process may be incorporated into the channel 101, as discussed above. The specific location of that layer 14 along any or all of the inner surfaces 120, 124, 140 of the channel 101 may be modified in an embodiment of the carrier that has one or more insets located within the walls 102. For example, the low-temperature plastic layer 154 may not be provided along the wall(s) having the inset(s), or the layer 154 may extend along such wall(s) in those regions not having the inset(s).

In accordance with one embodiment of the present invention, there is provided a method of promoting weight loss and weight management using the intra-oral device provided herein, where the act of wearing and interacting with the intra-oral device in the mouth satisfies oral fixation instead of the act of eating. The intra-oral device can be inserted into the mouth whenever a person has the desire to eat, for example because of an emotion or experiences hunger. The intra-oral device may then be removed when the person determines that his or her desire to eat is extinguished.

While the intra-oral device is positioned in the user's mouth, the user may be tempted to "bite" and "grind" into the device, which may desirably satisfy the user's desire to chew food. Moreover, the resilient deformability of the dental engagement features 144, particularly the bite-pads 150, desirably allows the user to perform a normal chewing cycle while the carrier 100 is received within the user's mouth. As discussed above, the ridge 152 preferably increases resistance to lateral movement of the user's jaw during the normal chewing cycle, which desirably enhances the sensory feedback to the portions of the brain that regulate eating behavior as well as satiety and pleasure.

Moreover, by having the bite-pads 150 positioned and structured so as to apply maximum pressure to the first molars when the user is chewing on the carrier, as discussed above, as well as (or alternatively) by providing the above-discussed textural features in various locations on the carrier to stimulate tactile receptors in the mouth, the intra-oral device will desirably maximize neuronal inputs to the feedback circuitry responsible for modulating feeding behaviors. As discussed above, it is believed that the first molars of both dental arches are the primary teeth at the somatosensory level participating in the satiety feedback mechanism. Thus, by having the bite-pads 150 of the intra-oral device apply maximum pressure to the first molars, it is believed that the present invention will provide maximal neuronal input to the feedback circuitry responsible for modulating feeding behaviors.

Thus, the psychological appeal of a particular eating behavior, or the appetite satisfying property of chewing food, may desirably be sublimated by the user's interaction with the inserted intra-oral device, including chewing on it so as to repeatedly compress the bite-pads 150 of the dental engagement features 144. Moreover, the intra-oral device may also, because of its tactile and other properties, deceive the brain into interpreting it as food, thereby stimulating salivation, which is the first part of the digestion of food. Thus, a user's specific eating behavior of generating saliva and swallowing is satisfied by insertion of and interaction with the intra-oral device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for promoting weight management, comprising:
    instead of eating, positioning an intra-oral device over at least a portion of a first arch of teeth of a user when the user has a desire to eat, the intra-oral device including a carrier having a resiliently deformable protuberance along an outer surface of the carrier;
    wherein the carrier has an outside wall, an inside wall, and an occlusal wall connecting the outside wall to the inside wall; wherein the outside wall, the inside wall, and the occlusal wall together define a channel configured to receive the portion of the first arch of teeth; and wherein the protuberance is positioned along the occlusal wall so as to contact a first molar of a second arch of teeth of the user when the intra-oral device is positioned in an inserted position in which the channel receives the portion of the first arch of teeth, the protuberance being dimensioned so as to apply more pressure to the first molar of the second arch of teeth than to any adjacent teeth of the second arch of teeth when the user chews on the intra-oral device.

2. The method of claim 1, further comprising:
    chewing on the intra-oral device so as to deform the protuberance.

3. The method of claim 1, further comprising:
    removing the intra-oral device from the user's mouth when the user's desire to eat is extinguished.

4. The method of claim 1, wherein the carrier is U-shaped, such that the channel is configured to receive substantially the entire first arch of teeth.

5. The method of claim 1, wherein the protuberance comprises a bite-pad, and wherein a height that the bite-pad projects above the occlusal wall defines an arcuate path along a length of the bite-pad.

6. The method of claim 1, wherein the protuberance comprises a bite-pad, wherein a length of the bite-pad extends from an anterior end to a posterior end of the bite-pad, and wherein the bite-pad is positioned and the length is dimensioned such that the anterior end is aligned with a second premolar of the second arch of teeth and the posterior end is aligned with a second molar of the second arch of teeth.

7. The method of claim 1, wherein the carrier further comprises a planar ridge.

8. The method of claim 7, wherein the planar ridge is located on a buccal side of the protuberance.

9. The method of claim 7, wherein the planar ridge projects above the outer surface to a height that is higher than a height that the protuberance projects above the occlusal wall.

10. The method of claim 1, wherein an outer surface of the protuberance has an uneven, textured surface.

11. The method of claim 10, wherein the textured surface is comprised of a plurality of dome-shaped nodules.

12. The method of claim 1, wherein the protuberance is comprised of a different material than the carrier, the protuberance comprising an elastomeric material, and the carrier comprising a polymer having a higher rigidity than the elastomeric material.

13. An intra-oral device, comprising:
a carrier having an outside wall, an inside wall, and an occlusal wall connecting the outside wall to the inside wall; wherein at least one of the outside wall, the inside wall, and the occlusal wall defines an outermost surface of the intra-oral device, and wherein the outside wall, the inside wall, and the occlusal wall together define a channel configured to receive at least a portion of a first arch of teeth of a user;
wherein the carrier has a plurality of resiliently deformable protuberances positioned along and projecting from the occlusal wall;
wherein a first one of the protuberances is a bite-pad, and
wherein a second one of the protuberances is a planar ridge extending alongside the bite-pad on a buccal side of the bite-pad, the planar ridge projecting above the occlusal wall to a height that is higher than a height that the bite-pad projects above the occlusal wall; and
wherein the bite-pad and the planar ridge are comprised of a different material than the outermost surface of the carrier, the bite-pad and the planar ridge comprising an elastomeric material, and the outermost surface of the carrier comprising a polymer having a higher rigidity than the elastomeric material.

14. The intra-oral device of claim 13, wherein an outer surface of at least one of the bite-pad and the planar ridge has an uneven, textured surface.

15. The intra-oral device of claim 13, wherein the plurality of protuberances are partially received within a recess in the outermost surface of the occlusal wall of the carrier.

* * * * *